US010182783B2

(12) United States Patent
Golan

(10) Patent No.: US 10,182,783 B2
(45) Date of Patent: Jan. 22, 2019

(54) VISUALIZATION OF EXPOSURE INDEX VALUES IN DIGITAL RADIOGRAPHY

(71) Applicant: CMT MEDICAL TECHNOLOGIES LTD, Yoqneam Ilit (IL)

(72) Inventor: Asaf Golan, Zikhron Ya'akov (IL)

(73) Assignee: CMT Medical Technologies Ltd., Yoqneam Ilit (IL)

( * ) Notice: Subject to any disclaimer, the term of this patent is extended or adjusted under 35 U.S.C. 154(b) by 0 days.

(21) Appl. No.: 14/857,603

(22) Filed: Sep. 17, 2015

(65) Prior Publication Data

US 2018/0110493 A1     Apr. 26, 2018

(51) Int. Cl.
| | |
|---|---|
| *A61B 6/00* | (2006.01) |
| *A61B 6/03* | (2006.01) |
| *G01T 1/17* | (2006.01) |
| *H04N 5/32* | (2006.01) |
| *G01N 23/223* | (2006.01) |
| *H01L 27/146* | (2006.01) |
| *H01L 31/08* | (2006.01) |
| *G01N 23/04* | (2018.01) |

(52) U.S. Cl.
CPC ............ *A61B 6/5241* (2013.01); *A61B 6/03* (2013.01); *A61B 6/5229* (2013.01); *G01N 23/04* (2013.01); *G01N 23/223* (2013.01); *G01T 1/17* (2013.01); *H01L 27/14663* (2013.01); *H01L 31/08* (2013.01); *H04N 5/32* (2013.01); *G01N 2223/1016* (2013.01); *G01N 2223/401* (2013.01)

(58) Field of Classification Search
None
See application file for complete search history.

(56) References Cited

U.S. PATENT DOCUMENTS

2006/0034536 A1*  2/2006  Ogren .................. G06T 7/0012
                                                        382/254

* cited by examiner

*Primary Examiner* — Hoon K Song
(74) *Attorney, Agent, or Firm* — Roach Brown McCarthy & Gruber, P.C.; Kevin D. McCarthy

(57) ABSTRACT

A method comprising: receiving a radiograph of at least a portion of a patient's body, wherein the radiograph is a digital grayscale image, and wherein each pixel of the grayscale image corresponds to a localized exposure index (EI) value; generating an HSL (Hue-Saturation-Lightness) image from the radiograph, wherein: a hue channel and a saturation channel of the HSL image are generated based on the localized EI values, a luminance channel of the HSL image is generated based on the intensity values of the pixels; and transforming the HSL image to an RGB image which conveys both the portion of the radiograph and the localized EI values.

20 Claims, 10 Drawing Sheets

VISUALIZATION OF EXPOSURE INDEX VALUES IN DIGITAL RADIOGRAPHY

FIELD OF THE INVENTION

The invention relates to the field of X-Ray imaging.

BACKGROUND

Digital radiographic imaging systems, such as those using photostimulable storage phosphor (PSP), amorphous selenium, amorphous silicon, charge-coupled device (CCD), and metal oxide semiconductor-field effect transistor (MOSFET) technology, can produce adequate image quality over a much broader range of exposure levels than that of screen/film imaging systems. In screen/film imaging, the final image brightness and contrast are indicative of over- and underexposure. In digital imaging, brightness and contrast are often determined entirely by digital post-processing of the acquired image data. Over- and underexposures are not readily recognizable.

In 2008, the International Electrotechnical Commission (IEC) developed and published International Standard IEC 62494-1, "Exposure Index of Digital X-Ray Imaging Systems", on the definition and scaling of the exposure index for digital radiography. According to the standard, the EI shall be proportional to the exposure (air kerma) and shall be scaled as EI=100*X, where X is the air kerma at the detector, at the calibration beam quality. The EI allows the operator to judge if an image was taken at a detector exposure level suitable for the intended level of image quality.

There is a significant degree of variability in the selection of exposure techniques to control X-ray exposure levels received by a patient undergoing an X-ray for diagnosis. Typically, the technologist visually assesses the thickness of the patient before making the selections. The combination of the patient thickness, the type of imaging receptor (e.g., computed radiography (CR), or digital radiography (DR)), and the choice of exposure techniques directly influences both the noise appearance and contrast in the captured image.

Once the image is captured, the technologist makes a visual assessment of the image quality, typically on a low-resolution, low-dynamic range monitor, and may also refer to the EI to determine if the image was properly exposed. The exposure indicator is a FIGURE of merit that is calculated for the captured image and that is related to the average signal level for the anatomical region of interest, prior to post-processing.

The technologist may decide to repeat the image if the EI is too low, or if the image appears noisy, i.e., if the image is deemed to be underexposed, or alternatively, may choose to modify the post-processing.

To reduce the number of images that may need to be repeated because of underexposure, and because there is some variability associated with the choice of exposure parameters, it is a typical practice to set the exposure parameters well-above the minimum level that is required to produce a diagnostic quality image. Consequently, patients that are imaged using standard x-ray machines may often receive a considerably higher radiation dose than that which is required for diagnosis. This can be a particular problem in intensive care units, where patients typically receive one or more chest x-rays per day, including pediatric and neonatal intensive care unit patients.

Hue-saturation-luminance models (HSL) typically map colors onto a three-dimensional prism-map comprising two symmetric cones stacked face-to-face. A given color may be thus described using cylindrical coordinates on the prism: the central vertical axis of the prism represents the luminance channel, the angle around the central vertical axis represents the hue, or chroma channel, and the distance from the central vertical axis to the surface of the prism represents the saturation channel Due to the conus-shape at either end of the prism, the range of the saturation channel depends on the luminance: in the middle of the range, the saturation channel provides a wide range of levels, whereas at the extrema comprising very dark or very light luminance values, the saturation channel provides a narrow range of levels. Additionally, human perception of different hues is not uniform—some hues, such as red hues, are perceptible over a wide range saturation levels, whereas other hues, such as blue hues, are perceptible over a narrower range of saturation levels. Thus, the surface of the HSL prism-map is not consistently convex, but includes bumps and dents.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a method comprising: receiving a radiograph of at least a portion of a patient's body, wherein the radiograph is a digital grayscale image, and wherein each pixel of the grayscale image corresponds to a localized exposure index (EI) value; generating an HSL (Hue-Saturation-Lightness) image from the radiograph, wherein: a hue channel and a saturation channel of the HSL image are generated based on the localized EI values, a luminance channel of the HSL image is generated based on the intensity values of the pixels; and transforming the HSL image to an RGB image which conveys both the portion of the radiograph and the localized EI values.

In some embodiments, the generated hue channel comprises: a first hue indicating a normal exposure range, a second hue indicating a deviation from the normal exposure range, and wherein the saturation channel comprises a lower saturation limit corresponding to the hue channel and the luminance channel, and wherein generating the HSL image further comprises: mapping pixels having a low exposure level within the normal exposure range to the first hue over a first luminance range, and mapping pixels having a high exposure level within the normal exposure range to the first hue over a second luminance range, and mapping pixels having a low exposure level within the deviation of the normal exposure range to the second hue over the first luminance range, and mapping pixels having a high exposure level within the deviation of the normal exposure range to the second hue over the second luminance range, and wherein the method further comprises applying an enhancement to the intensity values of the pixels, wherein the luminance channel of the HSL image is generated based on the enhanced intensity values, and wherein the enhancement comprises applying any combination of: an air segmentation, a saturation mask, a dynamic range compression, an adaptive S-curve to the radiograph, and balancing an intensity histogram of the radiograph with a standard intensity histogram.

In some embodiments, the method further comprises: a) receiving a target dose range corresponding to the normal exposure, and defining the transformation in accordance with the target dose range, and b) defining the transformation in accordance with a grayscale range of the radiograph, wherein mapping comprises applying a coherent filter to the EI value corresponding to a neighborhood of pixels.

In some embodiments, the generated hue channel comprises a third hue indicating an exposure level beyond the deviation from the normal exposure range, wherein generating the HSL image further comprises: mapping pixels having a low exposure level beyond the deviation of the normal exposure range to the third hue over the first luminance range, and mapping pixels having a high exposure level beyond the deviation of the normal exposure range to the third hue over the second luminance range, wherein mapping comprises defining multiple pivot points defining the respective boundaries of the normal exposure-range, the deviation from the normal exposure-range, and beyond the deviation from the normal exposure range, and applying a spline function to the pixels that are mapped between the pivot points.

In some embodiments, the method further comprises displaying at least a portion of the RGB image corresponding to a region of interest of the radiograph.

In some embodiments, the method further comprises calculating an adjusted radiation dosage level for applying to a subsequent imaging of the portion of the patient's body, wherein the subsequent imaging yields an EI level for the region of interest that lies within the normal exposure range.

In some embodiments, the method further comprises performing the receiving, generating and transforming steps for multiple sequential radiographs comprising a video stream of radiographs.

There is provided, in accordance with an embodiment, a computer program product comprising a non-transitory computer-readable storage medium having program code embodied thereon, the program code executable by at least one hardware processor to: receive a radiograph of at least a portion of a patient's body, wherein the radiograph is a digital grayscale image, and wherein each pixel of the grayscale image corresponds to a localized exposure index (EI) value; generate an HSL (Hue-Saturation-Lightness) image from the radiograph, wherein: a hue channel and a saturation channel of the HSL image are generated based on the localized EI values, a luminance channel of the HSL image is generated based on the intensity values of the pixels; and transform the HSL image to an RGB image which conveys both the portion of the radiograph and the localized EI values.

In some embodiments, the generated hue channel comprises: a first hue indicating a normal exposure range, a second hue indicating a deviation from the normal exposure range, and wherein the saturation channel comprises a lower saturation limit corresponding to the hue channel and the luminance channel, and wherein the program code is further executable to generate the HSL image by: mapping pixels having a low exposure level within the normal exposure range to the first hue over a first luminance range, and mapping pixels having a high exposure level within the normal exposure range to the first hue over a second luminance range, and mapping pixels having a low exposure level within the deviation of the normal exposure range to the second hue over the first luminance range, and mapping pixels having a high exposure level within the deviation of the normal exposure range to the second hue over the second luminance range, wherein the program code is further executable to apply an enhancement to the intensity values of the pixels, wherein the luminance channel of the HSL image is generated based on the enhanced intensity values, and wherein the enhancement comprises applying any combination of: an air segmentation, a saturation mask, a dynamic range compression, an adaptive S-curve to the radiograph, and balancing an intensity histogram of the radiograph with a standard intensity histogram.

In some embodiments, the program code is further executable to a) receive a target dose range corresponding to the normal exposure, and defining the transformation in accordance with the target dose range, and b) define the transformation in accordance with a grayscale range of the radiograph, wherein the program code is further executable to perform the mapping, comprising applying a coherent filter to the EI value corresponding to a neighborhood of pixels.

In some embodiments, the generated hue channel comprises a third hue indicating an exposure level beyond the deviation from the normal exposure range, and wherein the program code is further executable to generate the HSL image by: mapping pixels having a low exposure level beyond the deviation of the normal exposure range to the third hue over the first luminance range, and mapping pixels having a high exposure level beyond the deviation of the normal exposure range to the third hue over the second luminance range, and wherein the program code is further executable to perform the mapping, comprising defining multiple pivot points defining the respective boundaries of the normal exposure-range, the deviation from the normal exposure-range, and beyond the deviation from the normal exposure range, and applying a spline function to the pixels that are mapped between the pivot points.

In some embodiments, the program code is further executable to display at least a portion of the RGB image corresponding to a region of interest of the radiograph.

In some embodiments, the program code is further executable to calculate an adjusted radiation dosage level for applying to a subsequent imaging of the portion of the patient's body, wherein the subsequent imaging yields an EI level for the region of interest that lies within the normal exposure range.

In some embodiments, the program code is further executable to perform the receiving, generating and transforming steps for multiple sequential radiographs comprising a video stream of radiographs.

There is provided, in accordance with an embodiment, a system comprising: a radiography imaging apparatus configured to capture a radiograph of at least a portion of a patient's body, wherein the radiograph is a digital grayscale image, and wherein each pixel of the grayscale image corresponds to a localized exposure index (EI) value; and a hardware processor, configured to: receive the radiograph; generate an HSL (Hue-Saturation-Lightness) image from the radiograph, wherein: a hue channel and a saturation channel of the HSL image are generated based on the localized EI values, a luminance channel of the HSL image is generated based on the intensity values of the pixels; and transform the HSL image to an RGB image which conveys both the portion of the radiograph and the localized EI values.

In some embodiments, the generated hue channel comprises: a first hue indicating a normal exposure range, a second hue indicating a deviation from the normal exposure range, and wherein the saturation channel comprises a lower saturation limit corresponding to the hue channel and the luminance channel, and wherein the hardware processor is further configured to: a) generate the HSL image by: mapping pixels having a low exposure level within the normal exposure range to the first hue over a first luminance range, and mapping pixels having a high exposure level within the normal exposure range to the first hue over a second luminance range, and mapping pixels having a low exposure level within the deviation of the normal exposure range to the second hue over the first luminance range, and mapping pixels having a high exposure level within the deviation of the normal exposure range to the second hue over the second luminance range, and b) apply an enhancement to the intensity values of the pixels, wherein the luminance channel of the HSL image is generated based on the enhanced intensity values, and wherein the enhancement comprises applying any combination of: an air segmentation, a saturation mask, a dynamic range compression, an adaptive S-curve to the radiograph, and balancing an intensity histogram of the radiograph with a standard intensity histogram.

In some embodiments, the hardware processor is further configured to a) receive a target dose range corresponding to the normal exposure, and defining the transformation in accordance with the target dose range, and b) define the transformation in accordance with a grayscale range of the radiograph, wherein the hardware processor is further configured to perform the mapping, comprising applying a coherent filter to the EI value corresponding to a neighborhood of pixels.

In some embodiments, the generated hue channel comprises a third hue indicating an exposure level beyond the deviation from the normal exposure range, wherein the hardware processor is further configured to generate the HSL image by: mapping pixels having a low exposure level beyond the deviation of the normal exposure range to the third hue over the first luminance range, and mapping pixels having a high exposure level beyond the deviation of the normal exposure range to the third hue over the second luminance range, wherein the hardware processor is further configured to perform the mapping, comprising defining multiple pivot points defining the respective boundaries of the normal exposure-range, the deviation from the normal exposure-range, and beyond the deviation from the normal exposure range, and applying a spline function to the pixels that are mapped between the pivot points.

In some embodiments, the system further comprises a display monitor configured to render at least a portion of the RGB image corresponding to a region of interest of the radiograph.

In some embodiments, the hardware processor is further configured to calculate an adjusted radiation dosage level for applying to a subsequent imaging of the portion of the patient's body, wherein the subsequent imaging yields an EI level for the region of interest that lies within the normal exposure range.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

A system and method are disclosed to indicate one or more localized exposure index values (EI) on a radiograph of a patient's body, thereby allowing an operator to determine the quality and/or accuracy of the radiograph. The grayscale value (GL) corresponding to an EI value of the pixels of the radiograph are mapped onto a hue-saturation-lightness (HSL) scale to produce a single HSL image indicating both imaging information included in the radiograph as well as the localized EI levels. The HSL image is than transformed to a red-green-blue (RGB) scale for convenient viewing by the operator.

Figure 1:
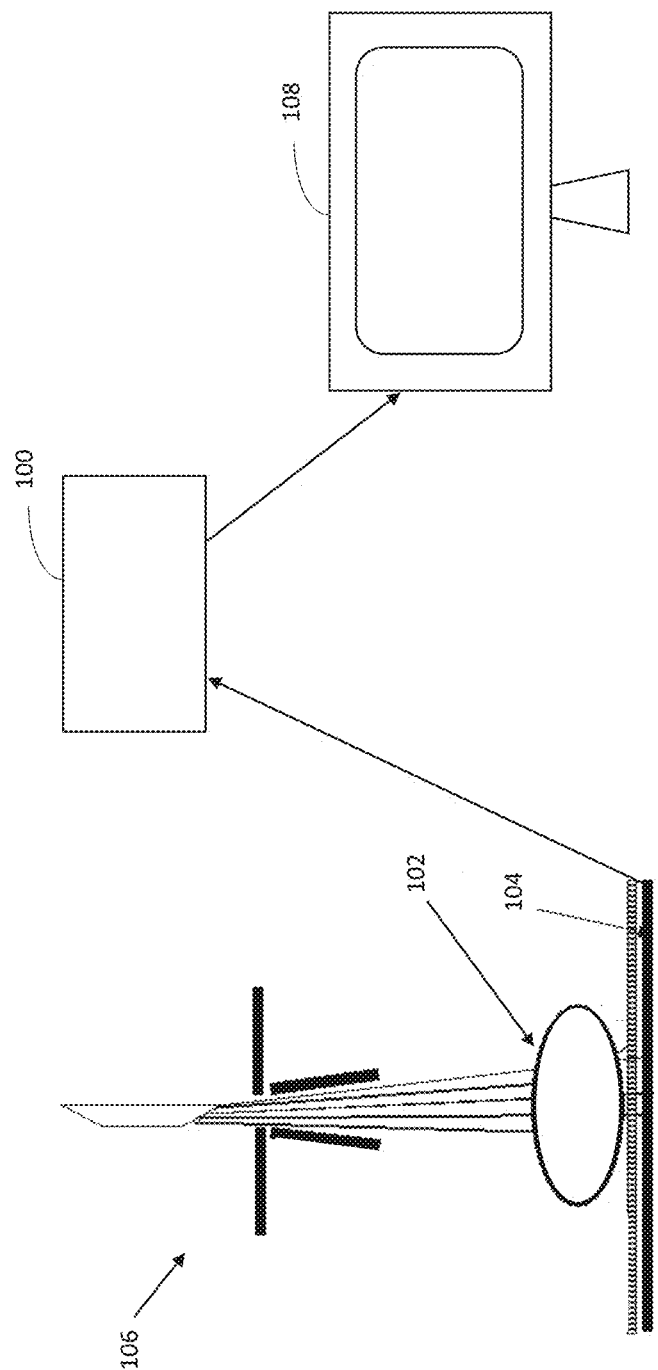
FIG. 1 illustrates a system to indicate localized exposure index levels (EI) of a radiograph via RGB imaging, in accordance with an embodiment.

Reference is made to FIG. 1 which illustrates a system to indicate localized EI exposure levels of a radiograph via RGB imaging. The system and method disclosed herein may be applied to a single radiograph, alternatively they may be applied to a video stream comprising multiple sequential radiographs. A hardware processor 100 receives a radiograph of bodily tissue 102, such as comprising a portion of a patient's body, captured by a detector 104 of a radiography imaging apparatus 106. Processor 100 may receive the radiograph using any suitable wired and/or wireless means, either remotely and/or locally.

Apparatus 106 may be an X-Ray machine, a CT (Computerized Tomography) machine, phosphor imaging device, or the like, as known in the art, for capturing radiographs and generating exposure index (EI) values. The radiograph may be a digital grayscale image where the gray level of each pixel of the radiograph corresponds to a localized EI value. Alternatively, gray level of a neighborhood of pixels corresponds to the localized EI value. Processor 100 generates an HSL (Hue-Saturation-Lightness) image from the radiograph, where:

a) a hue channel and a saturation channel of the HSL image are generated based on the localized EI values, and b) a luminance channel of the HSL image is generated based on the intensity values of the pixels.

Processor 100 transforms the HSL image to an RGB image using conventional methods, such as by transforming the HSL image to a Lab color-space which is then transformed to the RGB image. Processor 100 renders the RGB image on a display monitor 108 to convey both the grey scale resolution of the original radiograph, as well as a color mapping of the EI levels indicating a normal exposure range, a deviation from the normal exposure range, and optionally, an exposure level lying beyond the deviation. Optionally, a localized EI value may be displayed responsive to an indication of one or more points on the radiograph by the user, such as by having the user scroll over the image using a mouse. The transformed RGB image may be displayed superimposed, or side-by-side with the original radiograph. Alternatively, the RGB image corresponding to the ROI is superimposed on the rendered radiograph on monitor 108. Additionally, processor 100 may compute a regional EI value corresponding to the ROI, such as an average value, and display the regional EI value.

Processor 100 may define the hue channel to include at least two distinct hues, or chroma. One hue may indicate a normal exposure range, and a different hue may indicate a deviation from the normal exposure range. Optionally, processor 100 may use a third distinct hue to indicate an exposure range that lies beyond the deviation. Processor 100 may define one or more 'pivot points' that define the respective boundaries of the normal and deviation from the normal EI ranges, and the transition between the different hues in the HSL map corresponding to these pivot points. Pixels having EI values that lie between the pivot points may be mapped using a spline algorithm to smooth the transitions between the different hues and/or their saturation in the image.

An exemplary transformation of gray level scale to HSL values may be as follows: The gray scale may be divided into multiple ranges, each corresponding to one of the distinct hues. The middle GL range may correspond to the normal exposure range, such as may be defined by the clinic or hospital administering the X-ray treatment, and may be mapped onto the first hue. Grey levels within the defined deviation on either side of the normal EI range are mapped onto the second hue, where one range corresponds to below-normal exposure and the other range corresponds to above-normal exposure. For example, a target level may be set at 2.2 μG (micro-gray level), where 1 μG=157 GL (units of gray level scale) and 1 EI=100*GL/ (detector sensitivity). Thus the target set by the clinic may be 314 GL. A normal range may be defined as ±100 GL, giving a normal exposure range between 214 GL and 414 GL, centered about 314 GL. A deviation of 100 may be defined beyond the normal range, resulting in an above-normal exposure range between 414 GL and 514 GL, and a below-normal exposure range between 114 GL and 214 GL, both mapped onto the second hue. Ranges beyond the deviation may be defined for both high and low exposure levels and mapped onto the third hue: a very low exposure range between 0 to 114 GL, and a very high exposure range greater than 514 GL.

The pivot points are the values on the gray scale that correspond to a center of transition between the different hues. In the example, above, there are four pivot points on the grayscale at an EI of 214 GL and an EI of 414 GL corresponding to the transition between the first and second hues, and an EI of 114 GL, and an EI of 514 GL corresponding to the transition between the second and third hues. Thus, the pixels may be mapped to the different hues according to their EI values as indicated by the pivot points.

The luminance channel is used to further indicate the low or high EI values within a given hue range, as follows: low EI values may be mapped onto low luminance with high saturation for a given hue, and high EI values may be mapped onto high luminance with high saturation for the same hue, where the high saturation levels correspond to the luminance. Alternatively, EI levels may be mapped to the reverse luminance levels. Thus, the very low range with EI levels are mapped onto the third hue with low luminance and high saturation, the low deviation range between the very low range and the normal range is mapped onto the second hue with low luminance and high saturation, and the lower half EI levels of the normal range is mapped onto the first hue with low luminance and high saturation. Similarly, the upper half EI levels of the normal range is mapped onto the first hue with high luminance and high saturation, the high deviation range between the normal range and the very high range is mapped onto the second hue with high luminance and high saturation, and the very high range with is mapped onto the third hue with high luminance and high saturation.

The above mapping of EI values to HSL color scheme may be described as a path that traverses on or near the surface of an HSL prism-map. The path may begin at the third hue with a low luminance for the lowest EI levels, continue to the second hue with low luminance for the next lowest range of EI levels, and to the first hue with low luminance for lower half of the normal range. The path continues to the first hue with high luminance values for the higher half of the normal EI range, to the second hue with high luminance EI levels exceeding the normal range within the deviation, and to the third hue with high luminance for the highest EI levels lying beyond the deviation. The hues are selected to be neighbors in the color space, and therefore transitioning from one of the selected hues to another results in a continuous path that doesn't cross any additional hues.

A smoothing function, such as a spline may be applied when mapping pixels in the regions between the pivot points to obtain a higher quality image and smooth the transitions between the different hues in the color space.

The mapping may account for any hue or luminance-specific bulges or dents intrinsic to the prism-map to allow for uniform scaling across the different gray levels. Specifically, the saturation channel may be determined in accordance with the surface topology of the HSL prism-map.

Saturation values are determined for each mapped pixel according to a lower saturation limit corresponding to the hue channel and the luminance channel. The range of the saturation channel varies for different hue and lightness values, as represented by the two face-to-face cones comprising the HSL prism-map. In particular, for very high and/or low luminance values corresponding to at least some of the pivot points the saturation channel is typically small, corresponding to the tips of the cones. Thus, the pixels may be mapped to onto a saturation value that is substantially close to the maximum allowed saturation value for the corresponding mapped hue and luminance values.

Additionally, a nonlinear coherent filter may be applied to calculate the weighted sum of the localized EI values within a neighborhood of pixels and improve the resolution of the edges of the resulting HLS image. The weights may be dependent on the spatial distance between pixels and their intensity values. This allows calculating the EI values without being affected by edge transitions and/or noise.

A target dose range corresponding to the normal exposure range may be user-defined, such as from a technician, and may be specific to a hospital or clinic performing the imaging, and the transformation and the corresponding pivot points may be determined with reference to the received target dose range.

For example, the pivot point for the upper limit of the normal range may be determined by: GL(upper normal limit)=$10^{2/10}$*GLTarget for a target gray level of GLTarget. The remaining pivot points defining the boundaries between the different hues and saturation levels for the HLS color space may be similarly defined.

One or more enhancement techniques are applied to the intensity, or gray scale values of the pixels, and the luminance channel of the HSL image may be additionally, or optionally only, based on the enhanced intensity values, such as may include any combination of:

a. Applying a direct X-ray segmentation to the radiograph to differentiate between tissue and background, and discarding any portions of the radiograph that are associated with the background.

b. Applying a saturation mask on the radiograph and discarding pixels or regions whose gray level exceeds the saturation limit of the detector.
c. Balancing an intensity histogram representing the gray scale of the radiograph to fit a standard intensity histogram. This results in a consistent luminance map, expressed as the standard intensity histogram, for different radiographs having different intensity histograms. Balancing may include any of: applying a multiplier to the histogram of the radiograph to achieve automatic gain control, and applying an adaptive one-dimensional curve, such as a log-based curve, to the grayscale, or intensity values.
d. Applying a dynamic range compression, for example using a Gaussian pyramid, to compress the grayscale of the radiograph and sharpen the edges.
e. Applying an adaptive S-curve, such as a sigmoid curve or rotational-gamma curve, to the grayscale levels of the radiograph to adapt the color resolution to match the range of the display monitor, and window the image to the full dynamic range of the monitor.

These enhancements may be added to the mapping above.

Optionally, an adjusted radiation dosage level is calculated and presented for applying to a subsequent imaging to yield an EI level for the region of interest that lies within the normal exposure range. The red area of an RGB-mapped radiograph may be used to suggest an adjusted dosage level that will result in a green area for a subsequent image. The linear relationship between the Mas exposure levels to the resulting gray level may be leveraged to suggest a new Mas level that will yield the correct exposure level. For example, a radiograph of a shoulder may be taken at a dose of 70 Kilovolts (kV) at 8 milliamp*millisecond (mas), and the region of interest is indicated in red. The user may mark a region of interest (ROI), or alternatively, a pivot point indicating a transition between different hues and obtain the statistics, such as the average gray level, about the area of indication. In this example, the statistical average is a GL of 130. This value may be compared to the target GL of 300 that was set by the clinic. Since the Mas value has a linear association with the grey level, a new dose level may be determined to produce the desired target exposure level. Optionally, a predefined relationship of dosage levels to exposure levels, such as a calibration table, may be applied to adjust the dose accordingly. In the example, above, the dose may be adjusted to 72 kV and 12 mas.

Figure 3:
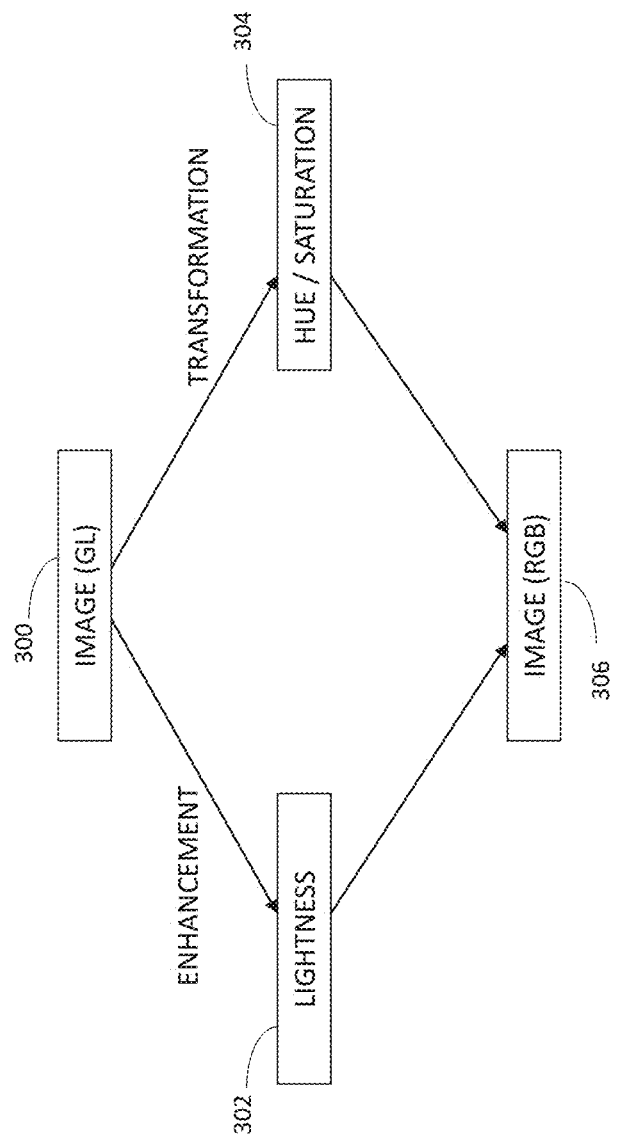
FIG. 3 shows a graphic depiction of an RGB mapping, in accordance with an embodiment.

Referring to FIG. 3, a graphic depiction of the RGB mapping above is shown. The radiograph is received as a greyscale image 300. The image undergoes one or more enhancements, as described above, to produce the lightness channel 302. Independently, the image undergoes one or more transformations to produce the hue and saturation channel 304, where the saturation is typically the highest available saturation corresponding to the respective luminance value. The lightness channel 302 and hue and saturation channel 304 are combined to produce the RGB image 306. The RGB colorspace may be any suitable absolute color space, such as sRGB, or Adobe RGB.

Reference is now made to FIGS. 2A-H, which illustrate RGB images generated from radiograph, in accordance with an embodiment. Pixels displayed in green, defined as the first hue, correspond to a normal exposure of a bodily tissue, pixels displayed in yellow, defined as the second hue, correspond to a deviation from the normal exposure range, and pixels displayed in red, defined as the third hue, correspond to exposure levels that lie beyond the deviation. High luminance and high saturation corresponds to high exposure, and low luminance and high saturation corresponds to low exposure.

Figure 2B:
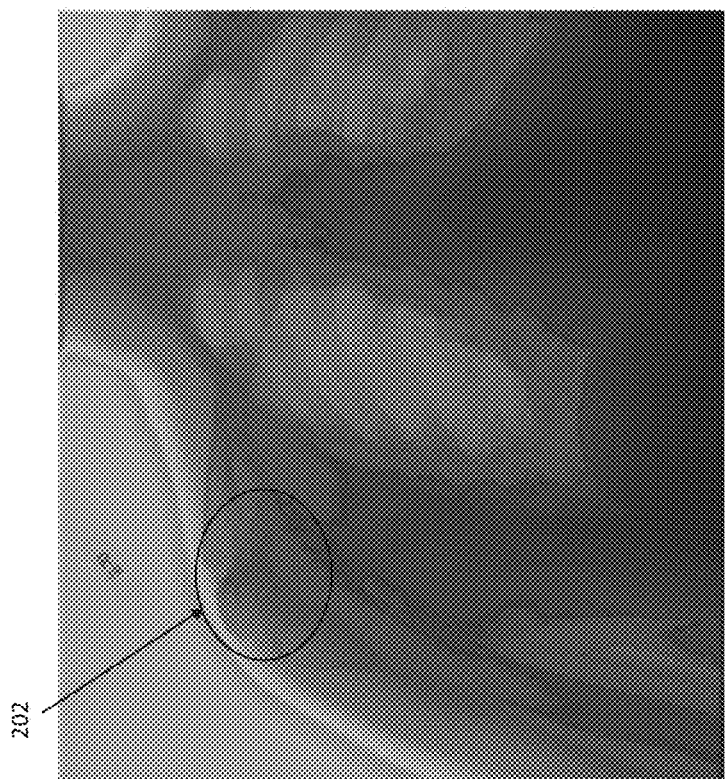
FIGS. 2A-H illustrate RGB images generated from radiograph, in accordance with an embodiment.
Figure 2A:
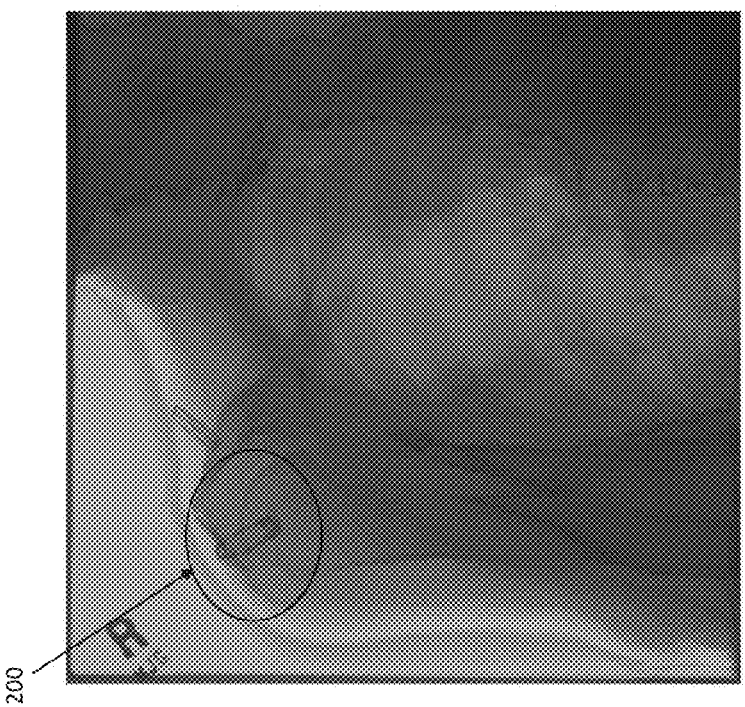

Referring to FIG. 2A, a ROI 200 comprising a portion of a shoulder is displayed in green, indicating that ROI 200 was correctly exposed, and that the radiograph is reliable.

Referring to FIG. 2B, much of this image is dark red, indicating an incorrect (low) exposure of these regions. However, most of a ROI 202 is displayed in green, thus the relevant part of the image received the correct exposure, despite incorrect exposure of other sections, and an overall EI value indicating insufficient exposure. Thus, the radiograph corresponding to this RGB image may suffice, precluding subjecting the patient to additional radiation resulting from retaking the radiograph.

Figure 2C:
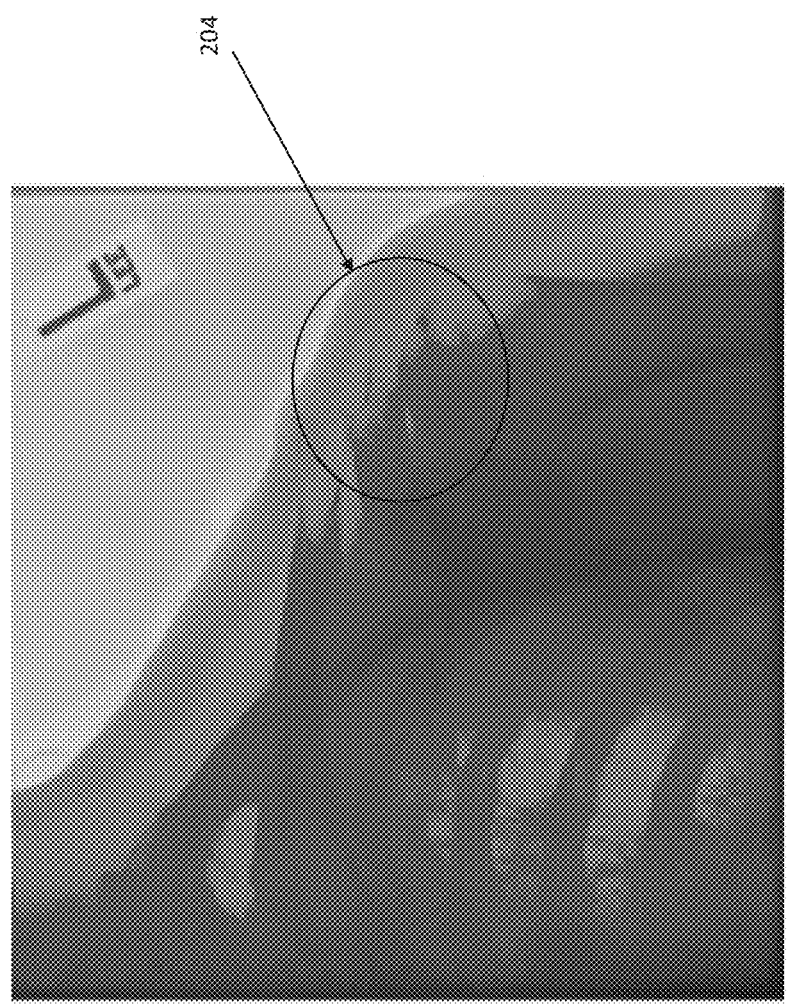

Referring to FIG. 2C, as with FIG. 2B, many of the pixels are red indicating incorrect exposure. A ROI 204 is displayed in red, indicating that ROI 204 received an incorrect exposure, and the radiograph associated with this RGB image has been incorrectly exposed. The operator may use the luminance values to determine if the exposure was too high or too low and adjust the exposure setting accordingly. For example, much of the red region in and around the ROI is relatively dark, indicating low luminance, corresponding to low exposure. Alternatively, a corrective exposure level may be computed as described above and presented to the operator.

Figure 2D:
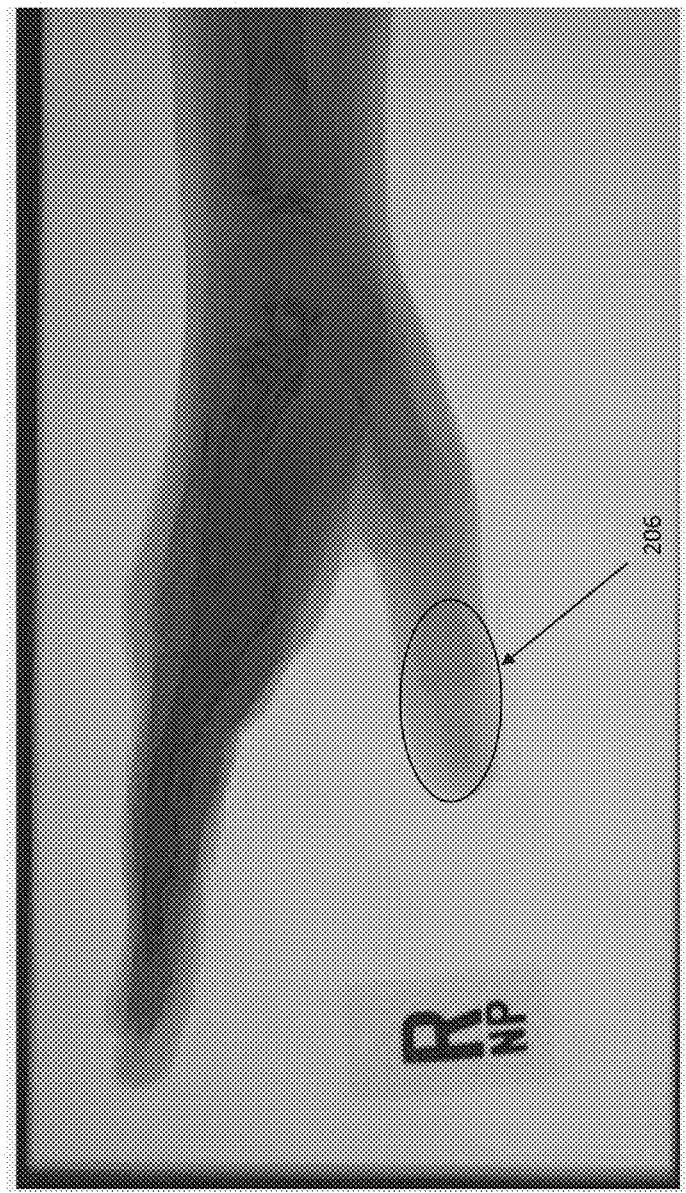

Referring to FIG. 2D, the overall EI value of this image indicates an incorrect exposure, however, the region of interest 206 (thumb) is displayed in green, and thus the radiograph associated with this RGB image is reliable and therefore does not need to be retaken. Although the technician may only have a low-resolution and/or low dynamic range monitor to view the radiograph, the RGB image readily indicates if the exposure at a given region of interest is correct or not.

Figure 2F:
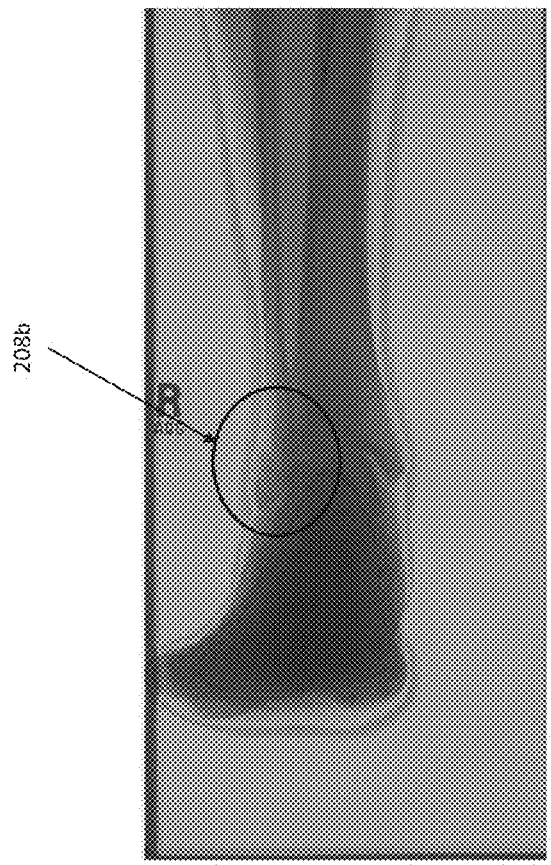
Figure 2E:
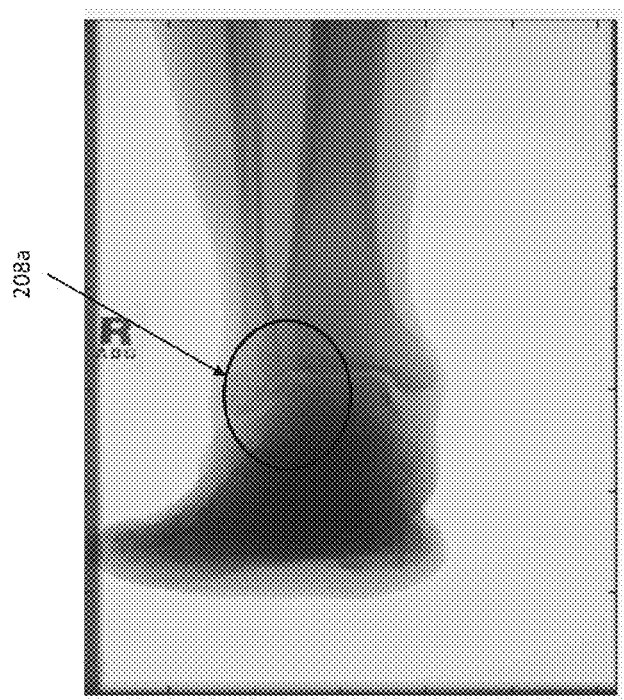

Referring to FIG. 2E, a radiograph of an ankle is shown. The position of the ankle appears problematic for diagnosing the ROI 208a FIG. 2F shows an RGB-mapped image of a radiograph similar to that shown in FIG. 2E. ROI 208b of FIG. 2E is indicated in green, and has therefore been correctly exposed. Thus, notwithstanding the problematic orientation of the ankle inferring that the image may not be reliable, the green indication of the ROI indicates that this image is, in fact, reliable. One or more post-processing methods may be applied to the image to better discern any features, as necessary.

Figure 2G:
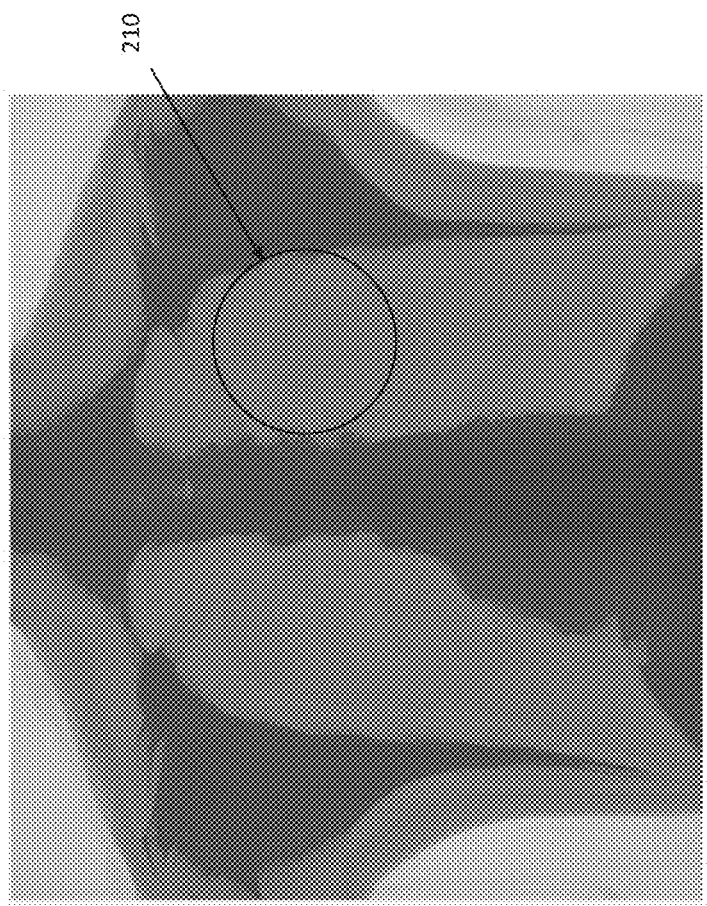

Referring to FIG. 2G, a typical chest image is shown. Much of this RGB image is shown in red indicating an incorrect exposure setting. Additionally, the overall EI level for the radiograph (not shown) indicates an incorrect exposure. However, a ROI 210 in the lungs is displayed in green, thus the associated radiograph image is reliable. Chest X-rays typically require segmentation of the lungs region to determine EI levels. By mapping to RGB, segmentation and any ensuing errors may be avoided.

Figure 2H:
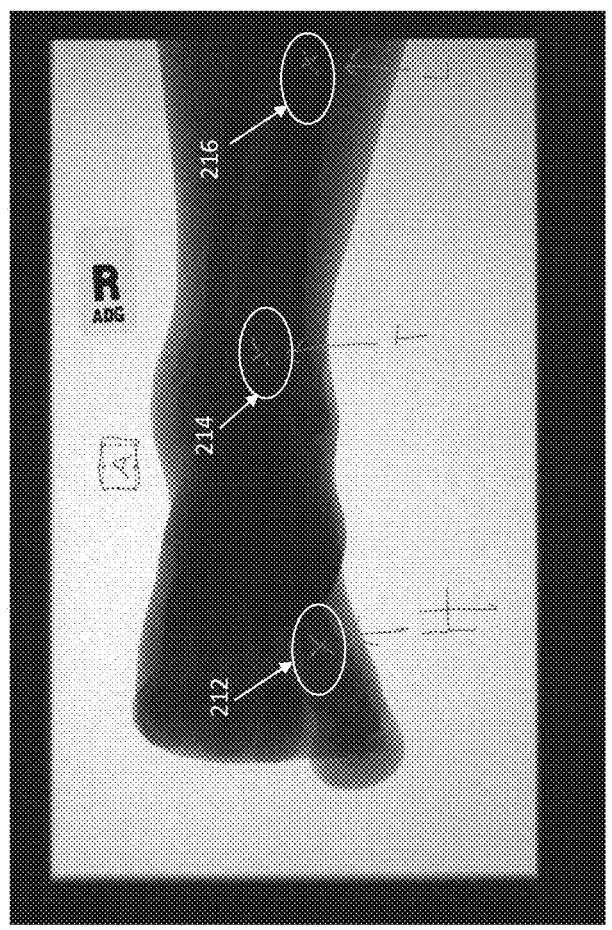

Reference is now made to FIG. 2H, which illustrates a radiograph of a foot. FIG. 2H shows a high exposure region 212, a normally exposed region 214, and a low exposure region 216. As can readily be seen in this radiograph, a single EI value is inadequate for evaluating the exposure level of the image.

Figure 4A:
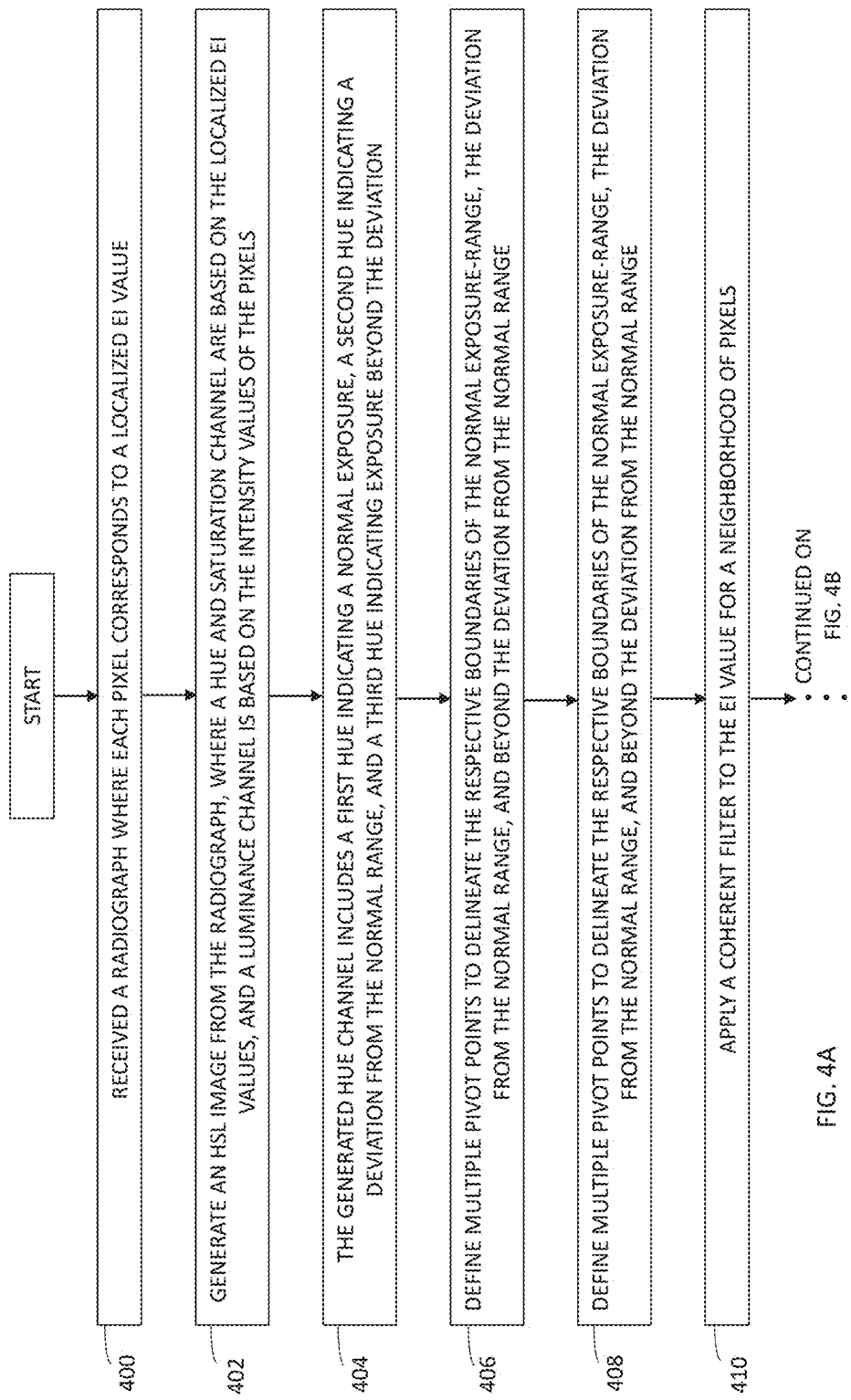
FIGS. 4A-B together, are a flowchart of a method for indicating one or more localized EI values on a radiograph of a patient's body, in accordance with an embodiment.
Figure 4B:
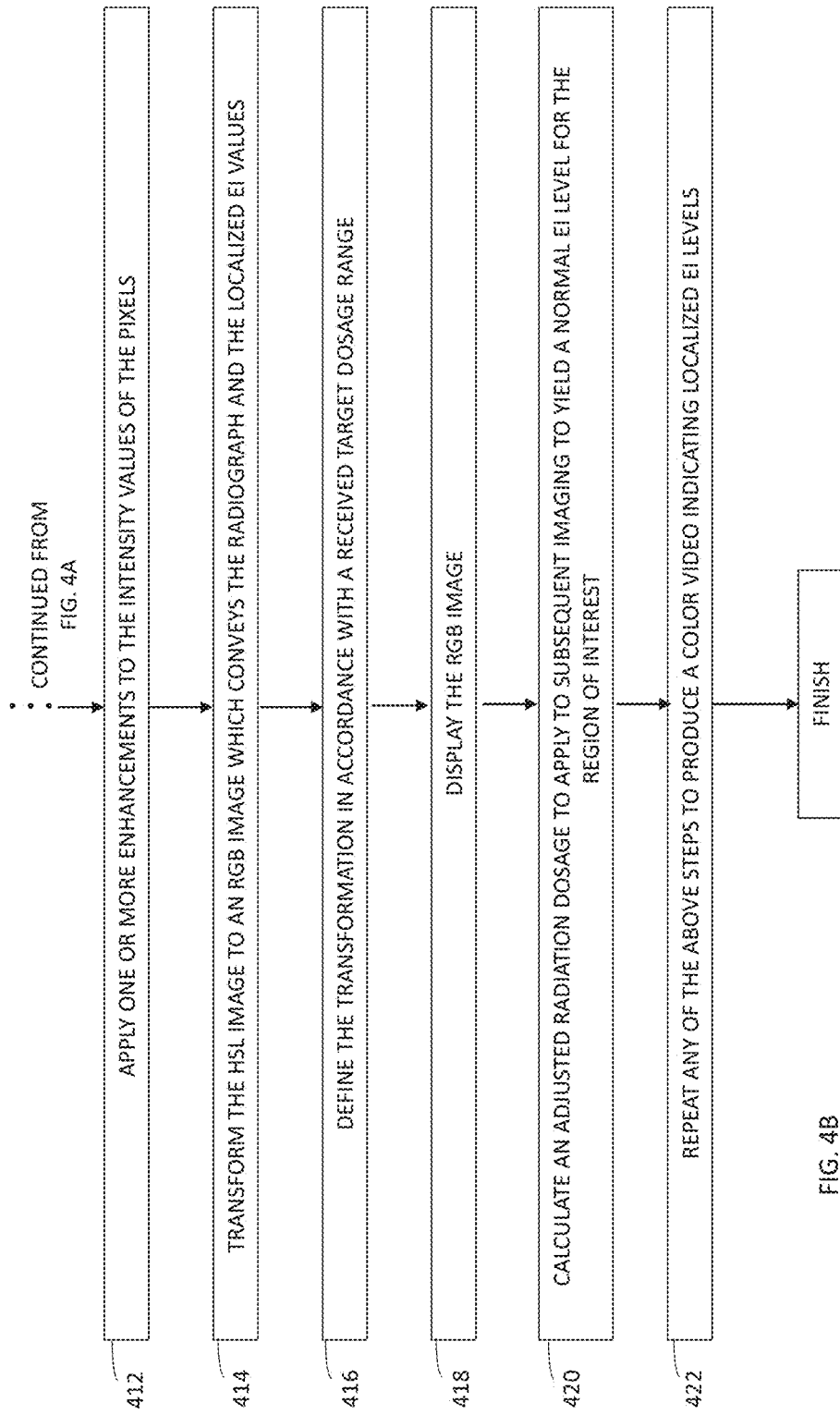

Reference is now made to FIGS. 4A-B which, together, are a flowchart of a method for indicating one or more localized EI values on a radiograph of a patient's body. A digital grayscale image, or radiograph, of at least a portion of a patient's body is received, where each pixel of the grayscale image corresponds to a localized EI value (Step 400). An HSL image from the radiograph is generated, where a hue channel and a saturation channel of the HSL image are generated based on the localized EI values, and a luminance channel of the HSL image is generated based on the intensity values of the pixels (Step 402).

The generated hue channel may comprise a first hue indicating a normal exposure range, a second hue indicating a deviation from the normal exposure range, and a third hue indicating an exposure level beyond the deviation from the normal exposure range (Step 404). Multiple pivot points may be defined to delineate the respective boundaries of the normal exposure-range, the deviation from the normal exposure-range, and beyond the deviation from the normal exposure range (Step 406).

The pixels may be mapped onto the hue and luminance channels using the pivot points (Step 408), as follows: Pixels having a low exposure level within the normal exposure range are mapped over a first luminance range to the first hue, as defined by the pivot points. Pixels having a high exposure level within the normal exposure range are mapped over a second luminance range to the first hue, as defined by the pivot points. Pixels having a low exposure level within the deviation of the normal exposure range are mapped over the first luminance range to the second hue, as defined by the pivot points. Pixels having a high exposure level within the deviation of the normal exposure range are mapped over the second luminance range to the second hue, as defined by the pivot points. Pixels having a low exposure level beyond the deviation of the normal exposure range are mapped over the first luminance range to the third hue, as defined by the pivot points. Pixels having a high exposure level beyond the deviation of the normal exposure range are mapped over the second luminance range to the third hue, as defined by the pivot points. A spline function may be applied to the pixels that are mapped between any of the pivot points.

Additionally, a coherent filter may be applied to the EI value corresponding to a neighborhood of pixels (Step 410). Optionally, one or more enhancement techniques comprising any combination of: an air segmentation, a saturation mask, balancing an intensity histogram of the radiograph with a standard intensity histogram, a dynamic range compression, and an adaptive S-curve to the radiograph, may be applied to the intensity values of the pixels, and the luminance channel of the HSL image may be generated based on the enhanced intensity values (Step 412).

The saturation channel may comprise a lower saturation limit corresponding to the hue channel and the luminance channel. The HSL image may be transformed in accordance with a grayscale range of the radiograph to an RGB image which conveys both the portion of the radiograph and the localized EI values (Step 414). The transformation may be defined in accordance with a received target dose range (Step 416).

The RGB image may be displayed (Step 418). Alternatively, a portion of the RGB image corresponding to a region of interest of the radiograph may be displayed. An adjusted radiation dosage level may be calculated for applying to a subsequent imaging of the portion of the patient's body, where the subsequent imaging may yield an EI level lying within the normal exposure range for the region of interest (Step 420).

The above described system and method may be applied to a stream of multiple sequential radiographs, such as a radiograph video, to produce a color video indicating localized EI levels, and therefore, applied dosage levels (Step 422). This may be useful for system calibration, developing a strategy for applying radiation dosages, and on-going quality measurements to adjust various X-ray parameters for fluoroscopic systems.

The present invention may be a system, a method, and/or a computer program product. The computer program product may include a computer readable storage medium (or media) having computer readable program instructions thereon for causing a processor to carry out aspects of the present invention.

The computer readable storage medium can be a non-transitory, tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention may be described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
receiving a radiograph of at least a portion of a patient's body, wherein the radiograph is a digital grayscale image, and wherein each pixel of the grayscale image corresponds to a localized exposure index (EI) value;
generating an HSL (Hue-Saturation-Lightness) image from the radiograph, wherein:
a hue channel and a saturation channel of the HSL image are generated based on the localized EI values,
a luminance channel of the HSL image is generated based on the intensity values of the pixels; and
transforming the HSL image to an RGB image which conveys both the portion of the radiograph and the localized EI values.

2. The method according to claim 1, wherein:
the generated hue channel comprises:
a first hue indicating a normal exposure range,
a second hue indicating a deviation from the normal exposure range, and
wherein the saturation channel comprises a lower saturation limit corresponding to the hue channel and the luminance channel, and wherein generating the HSL image further comprises:
mapping pixels having a low exposure level within the normal exposure range to the first hue over a first luminance range, and
mapping pixels having a high exposure level within the normal exposure range to the first hue over a second luminance range, and
mapping pixels having a low exposure level within the deviation of the normal exposure range to the second hue over the first luminance range, and
mapping pixels having a high exposure level within the deviation of the normal exposure range to the second hue over the second luminance range, and
wherein the method further comprises applying an enhancement to the intensity values of the pixels, wherein the luminance channel of the HSL image is generated based on the enhanced intensity values, and wherein the enhancement comprises applying any combination of: an air segmentation, a saturation mask, a dynamic range compression, an adaptive S-curve to the radiograph, and balancing an intensity histogram of the radiograph with a standard intensity histogram.

3. The method of claim 2, further comprising:
a) receiving a target dose range corresponding to the normal exposure, and defining the transformation in accordance with the target dose range, and
b) defining the transformation in accordance with a grayscale range of the radiograph,
wherein mapping comprises applying a coherent filter to the EI value corresponding to a neighborhood of pixels.

4. The method of claim 2, wherein the generated hue channel comprises a third hue indicating an exposure level beyond the deviation from the normal exposure range, wherein generating the HSL image further comprises:

mapping pixels having a low exposure level beyond the deviation of the normal exposure range to the third hue over the first luminance range, and mapping pixels having a high exposure level beyond the deviation of the normal exposure range to the third hue over the second luminance range, wherein mapping comprises defining multiple pivot points defining the respective boundaries of the normal exposure-range, the deviation from the normal exposure-range, and beyond the deviation from the normal exposure range, and applying a spline function to the pixels that are mapped between the pivot points.

5. The method of claim 1, further comprising displaying at least a portion of the RGB image corresponding to a region of interest of the radiograph.

6. The method of claim 5, further comprising calculating an adjusted radiation dosage level for applying to a subsequent imaging of the portion of the patient's body, wherein the subsequent imaging yields an EI level for the region of interest that lies within the normal exposure range.

7. The method of claim 1, further comprising performing the receiving, generating and transforming steps for multiple sequential radiographs comprising a video stream of radiographs.

8. A computer program product comprising a non-transitory computer-readable storage medium having program code embodied thereon, the program code executable by at least one hardware processor to:

receive a radiograph of at least a portion of a patient's body, wherein the radiograph is a digital grayscale image, and wherein each pixel of the grayscale image corresponds to a localized exposure index (EI) value;

generate an HSL (Hue-Saturation-Lightness) image from the radiograph, wherein:
  a hue channel and a saturation channel of the HSL image are generated based on the localized EI values,
  a luminance channel of the HSL image is generated based on the intensity values of the pixels; and
transform the HSL image to an RGB image which conveys both the portion of the radiograph and the localized EI values.

9. The computer program product according to claim 8, wherein:

the generated hue channel comprises:
  a first hue indicating a normal exposure range,
  a second hue indicating a deviation from the normal exposure range, and
wherein the saturation channel comprises a lower saturation limit corresponding to the hue channel and the luminance channel, and wherein the program code is further executable to generate the HSL image by:
  mapping pixels having a low exposure level within the normal exposure range to the first hue over a first luminance range, and
  mapping pixels having a high exposure level within the normal exposure range to the first hue over a second luminance range, and
  mapping pixels having a low exposure level within the deviation of the normal exposure range to the second hue over the first luminance range, and
  mapping pixels having a high exposure level within the deviation of the normal exposure range to the second hue over the second luminance range,
wherein the program code is further executable to apply an enhancement to the intensity values of the pixels, wherein the luminance channel of the HSL image is generated based on the enhanced intensity values, and wherein the enhancement comprises applying any combination of: an air segmentation, a saturation mask, a dynamic range compression, an adaptive S-curve to the radiograph, and balancing an intensity histogram of the radiograph with a standard intensity histogram.

10. The computer program product according to claim 9, wherein the program code is further executable to
  a) receive a target dose range corresponding to the normal exposure, and defining the transformation in accordance with the target dose range, and
  b) define the transformation in accordance with a grayscale range of the radiograph,
wherein the program code is further executable to perform the mapping, comprising applying a coherent filter to the EI value corresponding to a neighborhood of pixels.

11. The computer program product according to claim 9, wherein the generated hue channel comprises a third hue indicating an exposure level beyond the deviation from the normal exposure range, and wherein the program code is further executable to generate the HSL image by:
  mapping pixels having a low exposure level beyond the deviation of the normal exposure range to the third hue over the first luminance range, and
  mapping pixels having a high exposure level beyond the deviation of the normal exposure range to the third hue over the second luminance range, and
wherein the program code is further executable to perform the mapping, comprising defining multiple pivot points defining the respective boundaries of the normal exposure-range, the deviation from the normal exposure-range, and beyond the deviation from the normal exposure range, and applying a spline function to the pixels that are mapped between the pivot points.

12. The computer program product according to claim 8, wherein the program code is further executable to display at least a portion of the RGB image corresponding to a region of interest of the radiograph.

13. The computer program product according to claim 12, wherein the program code is further executable to calculate an adjusted radiation dosage level for applying to a subsequent imaging of the portion of the patient's body, wherein the subsequent imaging yields an EI level for the region of interest that lies within the normal exposure range.

14. The computer program product according to claim 8, wherein the program code is further executable to perform the receiving, generating and transforming steps for multiple sequential radiographs comprising a video stream of radiographs.

15. A system comprising:
a radiography imaging apparatus configured to capture a radiograph of at least a portion of a patient's body, wherein the radiograph is a digital grayscale image, and wherein each pixel of the grayscale image corresponds to a localized exposure index (EI) value; and
a hardware processor, configured to:
  receive the radiograph;
  generate an HSL (Hue-Saturation-Lightness) image from the radiograph, wherein:
    a hue channel and a saturation channel of the HSL image are generated based on the localized EI values,
    a luminance channel of the HSL image is generated based on the intensity values of the pixels; and
  transform the HSL image to an RGB image which conveys both the portion of the radiograph and the localized EI values.

16. The system of claim 15, wherein:
the generated hue channel comprises:

a first hue indicating a normal exposure range,
a second hue indicating a deviation from the normal exposure range, and
wherein the saturation channel comprises a lower saturation limit corresponding to the hue channel and the luminance channel, and
wherein the hardware processor is further configured to:
a) generate the HSL image by:
mapping pixels having a low exposure level within the normal exposure range to the first hue over a first luminance range, and
mapping pixels having a high exposure level within the normal exposure range to the first hue over a second luminance range, and
mapping pixels having a low exposure level within the deviation of the normal exposure range to the second hue over the first luminance range, and
mapping pixels having a high exposure level within the deviation of the normal exposure range to the second hue over the second luminance range, and
b) apply an enhancement to the intensity values of the pixels, wherein the luminance channel of the HSL image is generated based on the enhanced intensity values, and wherein the enhancement comprises applying any combination of: an air segmentation, a saturation mask, a dynamic range compression, an adaptive S-curve to the radiograph, and balancing an intensity histogram of the radiograph with a standard intensity histogram.

17. The system of claim 16, wherein the hardware processor is further configured to
a) receive a target dose range corresponding to the normal exposure, and defining the transformation in accordance with the target dose range, and
b) define the transformation in accordance with a grayscale range of the radiograph,
wherein the hardware processor is further configured to perform the mapping, comprising applying a coherent filter to the EI value corresponding to a neighborhood of pixels.

18. The system of claim 16, wherein the generated hue channel comprises a third hue indicating an exposure level beyond the deviation from the normal exposure range, wherein the hardware processor is further configured to generate the HSL image by:
mapping pixels having a low exposure level beyond the deviation of the normal exposure range to the third hue over the first luminance range, and
mapping pixels having a high exposure level beyond the deviation of the normal exposure range to the third hue over the second luminance range,
wherein the hardware processor is further configured to perform the mapping, comprising defining multiple pivot points defining the respective boundaries of the normal exposure-range, the deviation from the normal exposure-range, and beyond the deviation from the normal exposure range, and applying a spline function to the pixels that are mapped between the pivot points.

19. The system of claim 15, further comprising a display monitor configured to render at least a portion of the RGB image corresponding to a region of interest of the radiograph.

20. The system of claim 19, wherein the hardware processor is further configured to calculate an adjusted radiation dosage level for applying to a subsequent imaging of the portion of the patient's body, wherein the subsequent imaging yields an EI level for the region of interest that lies within the normal exposure range.

* * * * *